United States Patent
Yu et al.

(10) Patent No.: US 10,703,717 B2
(45) Date of Patent: Jul. 7, 2020

(54) WATER-SOLUBLE ISATIN DERIVATIVE, AND MANUFACTURING METHOD AND APPLICATION THEREOF

(71) Applicant: TIANJIN UNIVERSITY OF SCIENCE & TECHNOLOGY, Tianjin (CN)

(72) Inventors: Peng Yu, Tianjin (CN); Dong Wang, Tianjin (CN); Yuou Teng, Tianjin (CN); Longfei Miao, Tianjin (CN); Jing Wang, Tianjin (CN); Qian Zhang, Tianjin (CN); Yuan Yuan, Tianjin (CN)

(73) Assignee: Tianjin University of Science & Technology, Tianjin (CN)

( * ) Notice: Subject to any disclaimer, the term of this patent is extended or adjusted under 35 U.S.C. 154(b) by 97 days.

(21) Appl. No.: 16/089,968

(22) PCT Filed: Jul. 28, 2016

(86) PCT No.: PCT/CN2016/091979
§ 371 (c)(1),
(2) Date: Sep. 28, 2018

(87) PCT Pub. No.: WO2018/014368
PCT Pub. Date: Jan. 25, 2018

(65) Prior Publication Data
US 2019/0359568 A1    Nov. 28, 2019

(30) Foreign Application Priority Data
Jul. 20, 2016 (CN) ............................ 2016 1 0589432

(51) Int. Cl.
*C07D 209/38*   (2006.01)
*A61P 35/00*    (2006.01)
(52) U.S. Cl.
CPC ............ *C07D 209/38* (2013.01); *A61P 35/00* (2018.01)

(58) Field of Classification Search
CPC .............................. C07D 209/38; A61P 35/00
See application file for complete search history.

(56) References Cited

U.S. PATENT DOCUMENTS

2013/0225637 A1*  8/2013  Horne ................. C07D 401/04
                                                       514/339

FOREIGN PATENT DOCUMENTS

| CN | 104130175 A | 11/2014 |
| CN | 104130176 A | 11/2014 |

OTHER PUBLICATIONS

Xu, S. et al., "Synthesis and AChE Inhibitory Activity of Chalcones Mannich Base Derivatives," *Chinese J. Org. Chem.*, 34:749-755 (2013).
Hwang, D.R. et al., "A Modified Mannich-Type Reaction Catalyzed by VO (acac)2," *Org. Lett.*, 4(3):463-466 (2002).
An English translation of International Search Report of PCT/CN2016/091979 dated Apr. 26, 2017, WIPO.

* cited by examiner

*Primary Examiner* — Laura L Stockton
(74) *Attorney, Agent, or Firm* — Nixon & Vanderhye P.C.

(57) ABSTRACT

A novel type of water-soluble isatin derivatives, and manufacturing method and application thereof. An isatin derivative comprising a phenolic hydroxy group is used as the substrates. A dimethylaminomethylene group is introduced to an ortho position of the phenolic hydroxy group to significantly improve the water solubility of a class of compounds provided by the invention. An antitumor activity study showed that the activity of the class of compounds was not reduced, and even improved. The class of compounds has great prospects for applications in developing an antitumor pharmaceutical product.

14 Claims, 4 Drawing Sheets

WATER-SOLUBLE ISATIN DERIVATIVE, AND MANUFACTURING METHOD AND APPLICATION THEREOF

TECHNICAL FIELD

The invention belongs to the field of novel compound synthesis and drug application, and relates to a novel water-soluble isatin derivative, comprises synthesis, evaluation and application of these derivatives.

TECHNICAL BACKGROUND

Oxindole compound as nitrogen heterocyclic alkaloid, is widely distributed in nature, and has good biological activity, such as anti-tumor, anti-virus and antibacterial, reducing blood pressure, resisting cardiovascular and cerebrovascular diseases et al. The medicine containing the oxindole core structure is clinically used for treating tumors, inflammation, cardiovascular and cerebrovascular diseases and mental diseases. Representative derivatives are isatin (see FIG. 1), indirubin (see FIG. 1) and tetracyclic indolone alkaloids (see FIG. 1). Study shows that isatin is used as a lead compound for treatment of cancer to inhibit growth of various tumor cells, whereas it has no effect on normal cells, therefore the toxic and side effects of the anti-tumor drug are effectively reduced. These biological characteristics of the isatin derivatives not only inherit the advantages of the traditional Chinese medicine, but also overcome the drawbacks of the existing anticancer drug that would damage normal cells. However, literature reports that oxindole derivatives have poor water solubility, and the bioavailability is low, so the application of these compounds in clinical application is limited. Therefore, it has great significance to synthesize the oxindole derivatives with good water solubility and bioactivity.

Structures of oxindole derivatives

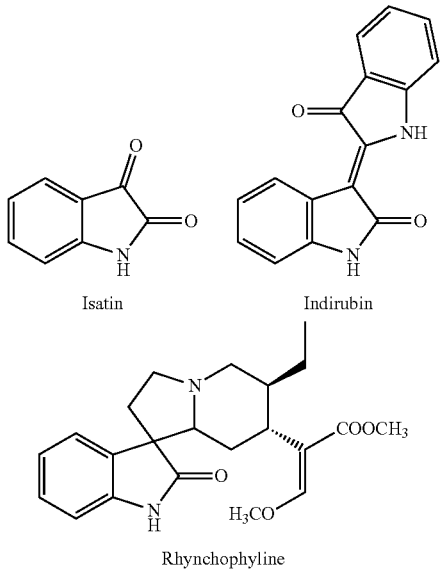

Isatin    Indirubin

Rhynchophyline

DESCRIPTION

The invention aims to provide structures and related synthetic methods of isatin derivatives containing phenolic hydroxyl groups with increased water solubility. Dimethylamine methylene group is introduced into the ortho-position of the phenolic hydroxyl group, so that the water solubility of the compound is remarkably improved, and the anti-tumor activity study shows that the activity is not reduced, some of which even has increased activity.

The objective of the invention is realized by the following technical scheme:

A novel water-soluble isatin derivative, having the following general structure:

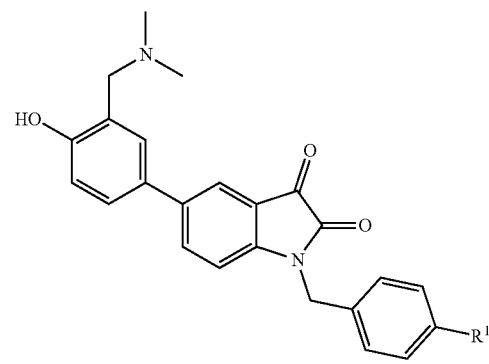

wherein $R^1$ is alkyl, alkoxy, trifluoromethyl or aryl.

A novel water-soluble isatin derivative, having the following general structure:

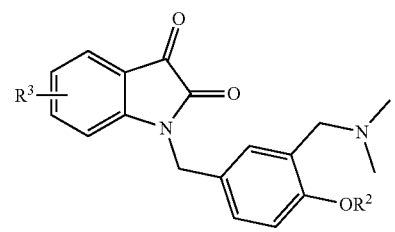

wherein, $R^2$ is hydrogen or alkyl, and $R^3$ is a group connected to any position of the benzene ring, wherein the group is an α, β-unsaturated ester group, an alkyl group, an alkoxy group, a halogen group, a carboxyl group, a cyano group or an aryl group.

The preparation method of the compound I according to claim 1, wherein the method comprises the following steps:

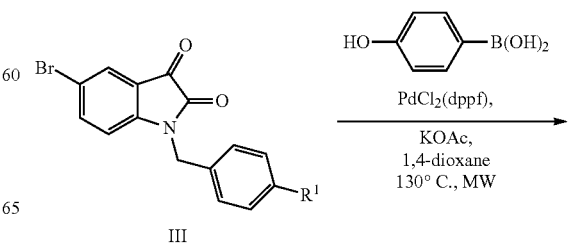

III

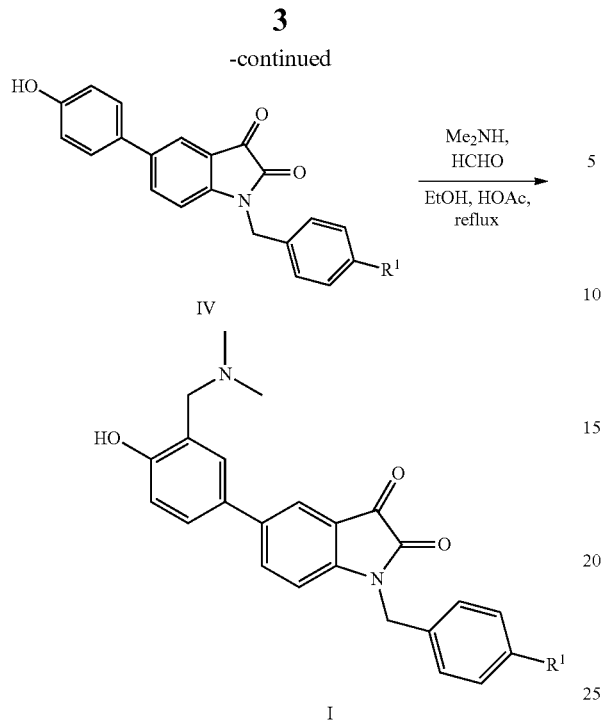

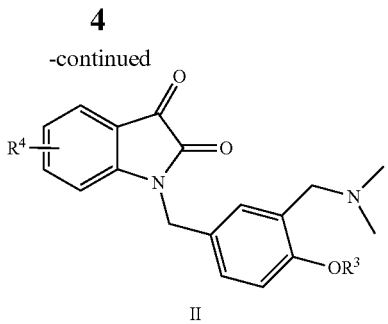

taking a known compound III as a starting material, converting compound III into compound IV by Suzuki coupling reaction; converting compound IV into the final product I through Mannich-like reaction with dimethyl amine, formaldehyde under the catalysis of acetic acid.

The preparation method of the compound II comprises the following steps:

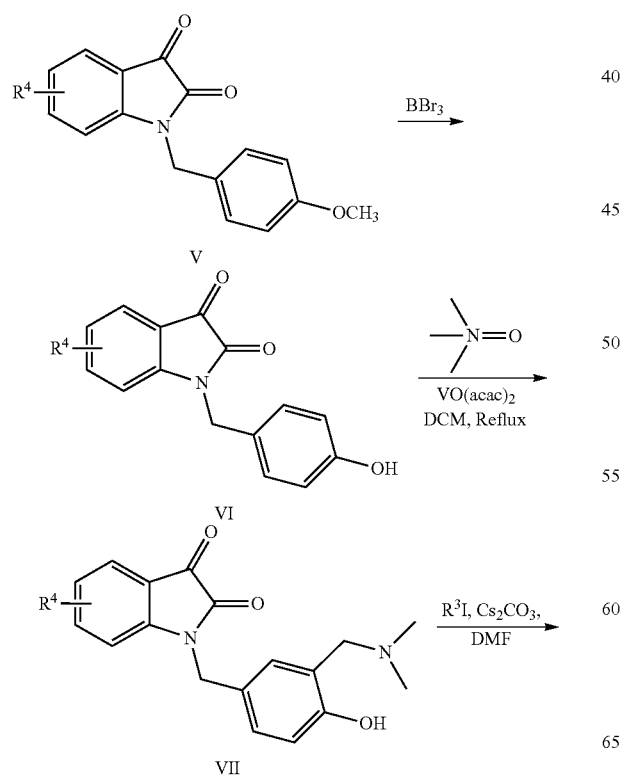

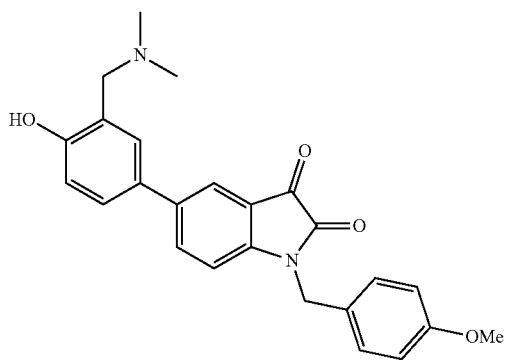

Taking the compound V as a raw material, removing methyl group under the action of boron tribromide to obtain VI, and then under the catalysis of a vanadium catalyst, reacting with trimethylamine nitrogen oxide to obtain VII, and finally reacting with an alkyl iodide $R^3I$ to obtain product II.

Novel oxindole derivatives containing dimethylamine methylene groups, having the following structure:

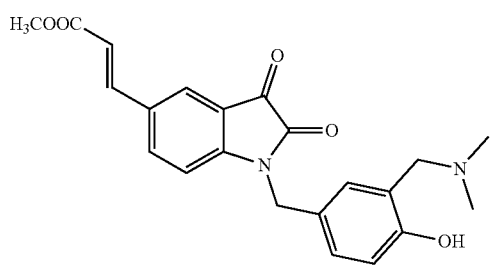

Novel oxindole derivatives containing dimethylamine methylene groups, having the following structure:

Use of the above novel isatin derivatives in improvement of water solubility

Use of the above novel water-soluble isatin for the preparation of a medicament for treating cancer or anti-tumor drugs.

In-vitro anti-tumor activity results of compounds 1, 2, 4 and 6 are shown in table 1 (compound 1, 2, 4 and 6 is shown in examples)

TABLE 1

| Compounds | Water solubility | K562 (IC$_{50}$, μM) | HepG2 (IC$_{50}$, μM) | HCT116 (IC$_{50}$, μM) |
|---|---|---|---|---|
| CPT | insoluble | 0.1~1 | 0.1~1 | 0.1~1 |
| 1 | >10 g/100 g | 1~10 | 1~10 | 1~10 |
| 2 | >10 g/100 g | <0.01 | 1~10 | <0.01 |
| 6 | insoluble | 0.01~0.1 | >10 | 0.01~0.1 |

The results of table 1 show that the water solubility of target compounds 1 and 2 is obviously improved. The compound 1 still retains certain cytotoxic activity. Compared with a precursor compound 6 of the compound 2, the activity of the compound 2 is greatly improved, and the activity is superior to that of a positive reference substance camptothecin; the anti-tumor effect is obvious.

The invention has the following advantages and positive effects:

(1) The invention designs a simple and convenient method capable of remarkably improving the water solubility of isatin derivatives, is suitable for various kinds of phenolic hydroxyl-containing drugs.

(2) The invention provides two synthetic methods for introducing dimethylamine methylene groups into ortho-positions of phenolic hydroxyl groups. The two methods have the advantages of simplicity and convenience in operation, cheap and easily available raw compounds, high yields, et al.

(3) The activity of all water-soluble isatin derivatives in anti-tumor aspect is not lower than that of parent compounds with poor water solubility, some of water-soluble isatin derivatives is slightly improved.

EXAMPLES

Figure 1:
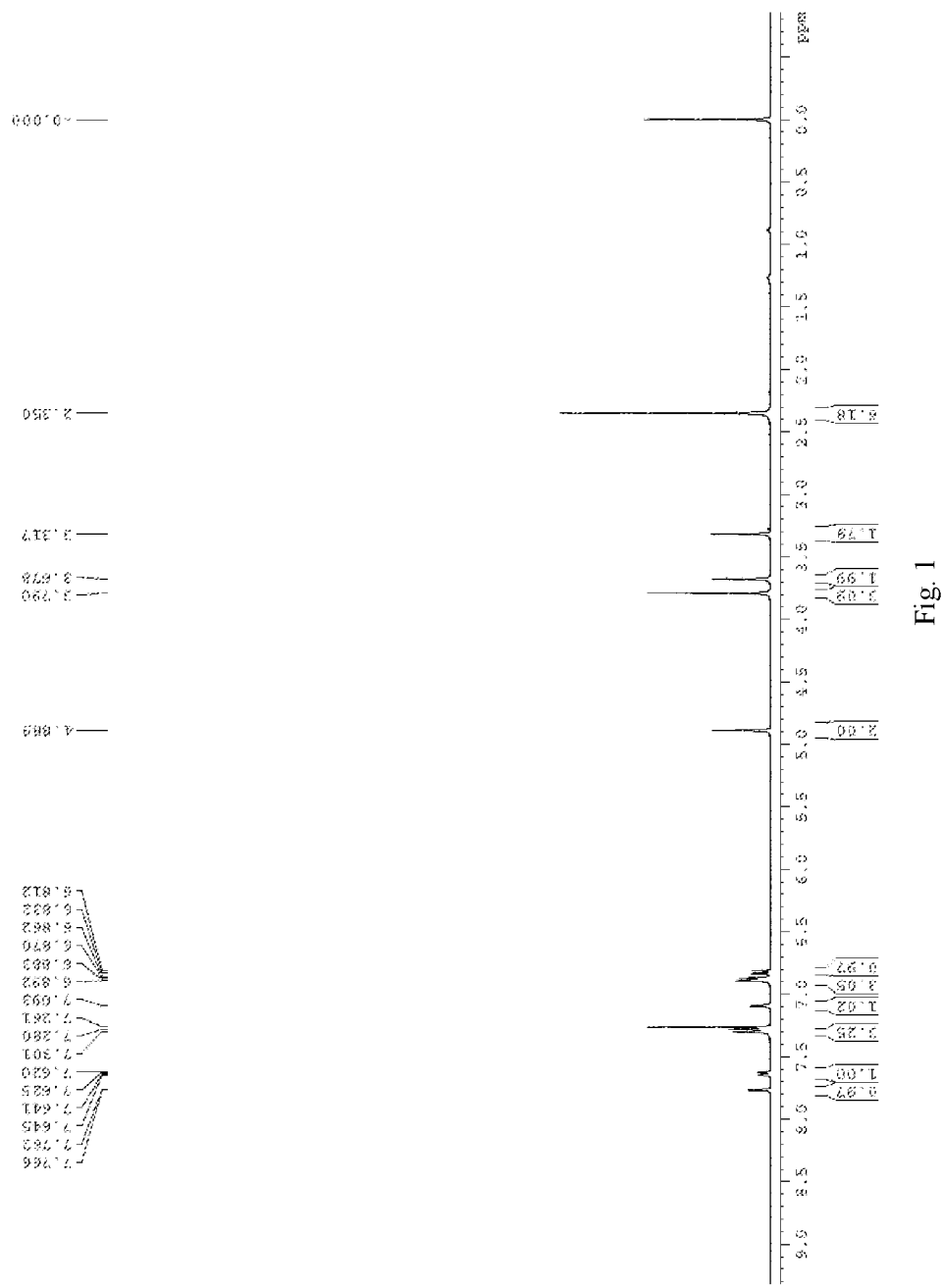
FIG. 1 is $^1$H NMR spectra of compound 1 in deuterated chloroform.
Figure 2:
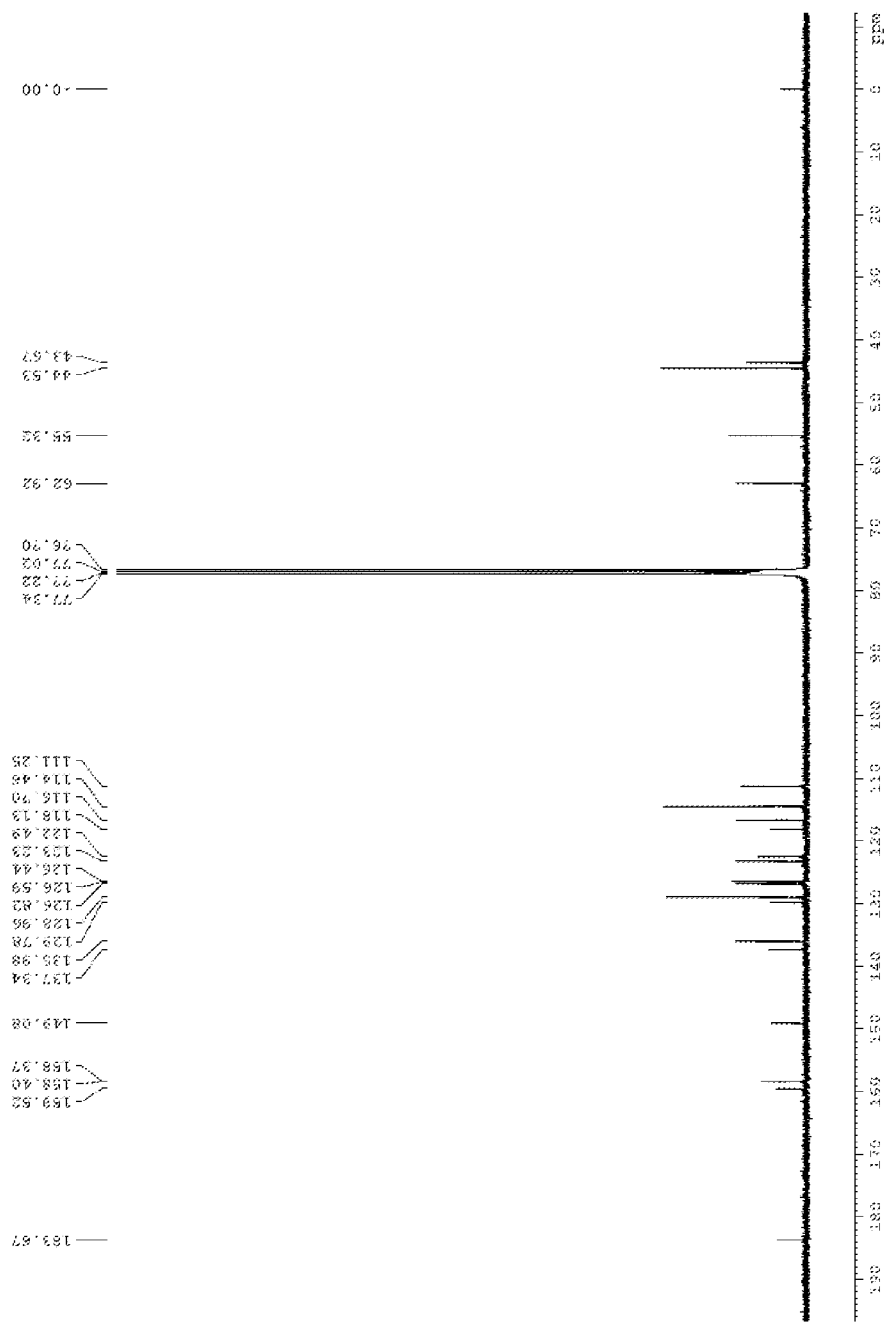
FIG. 2 is $^{13}$C NMR spectra of compound 1 in deuterated chloroform.
Figure 3:
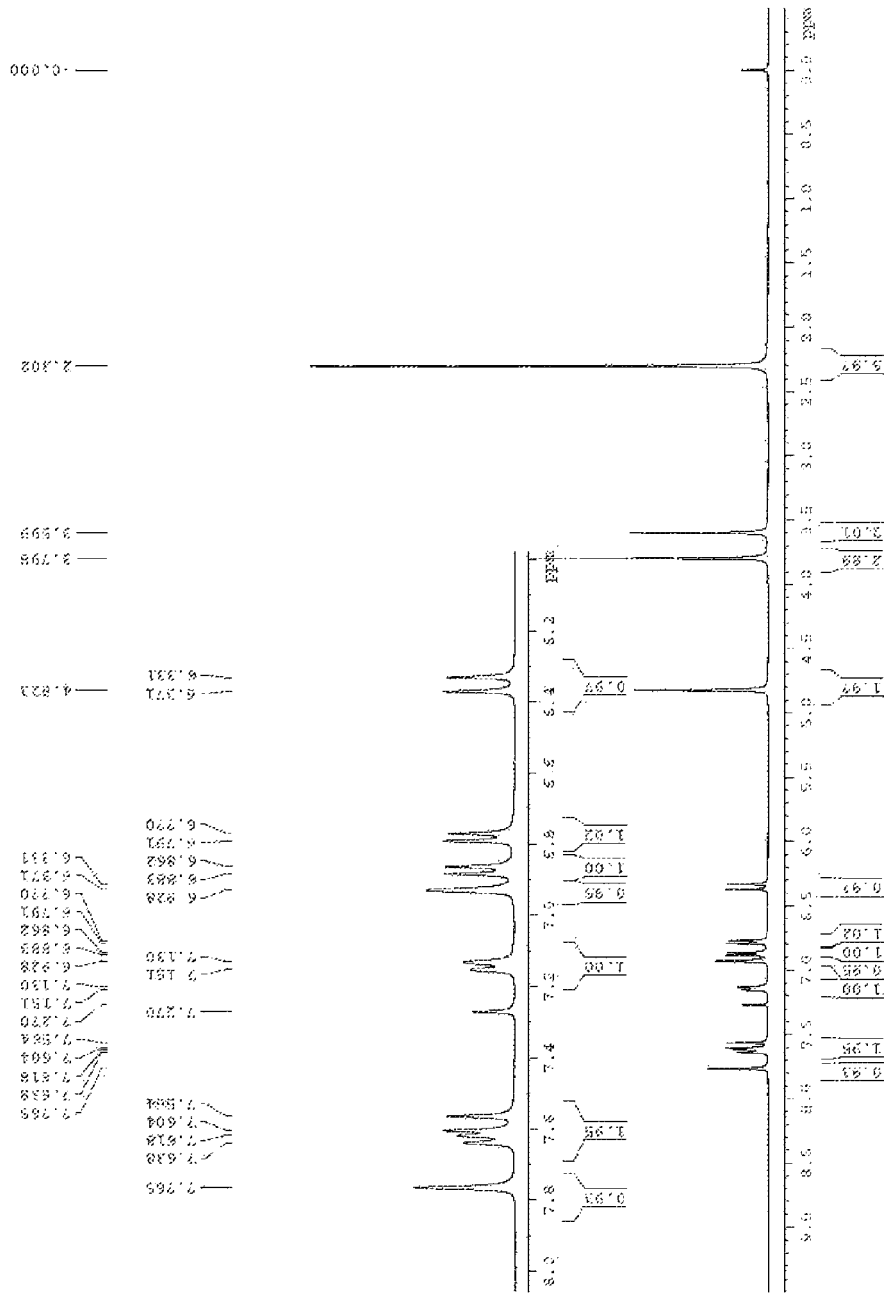
FIG. 3 is $^1$H NMR spectra of compound 2 in deuterated chloroform.
Figure 4:
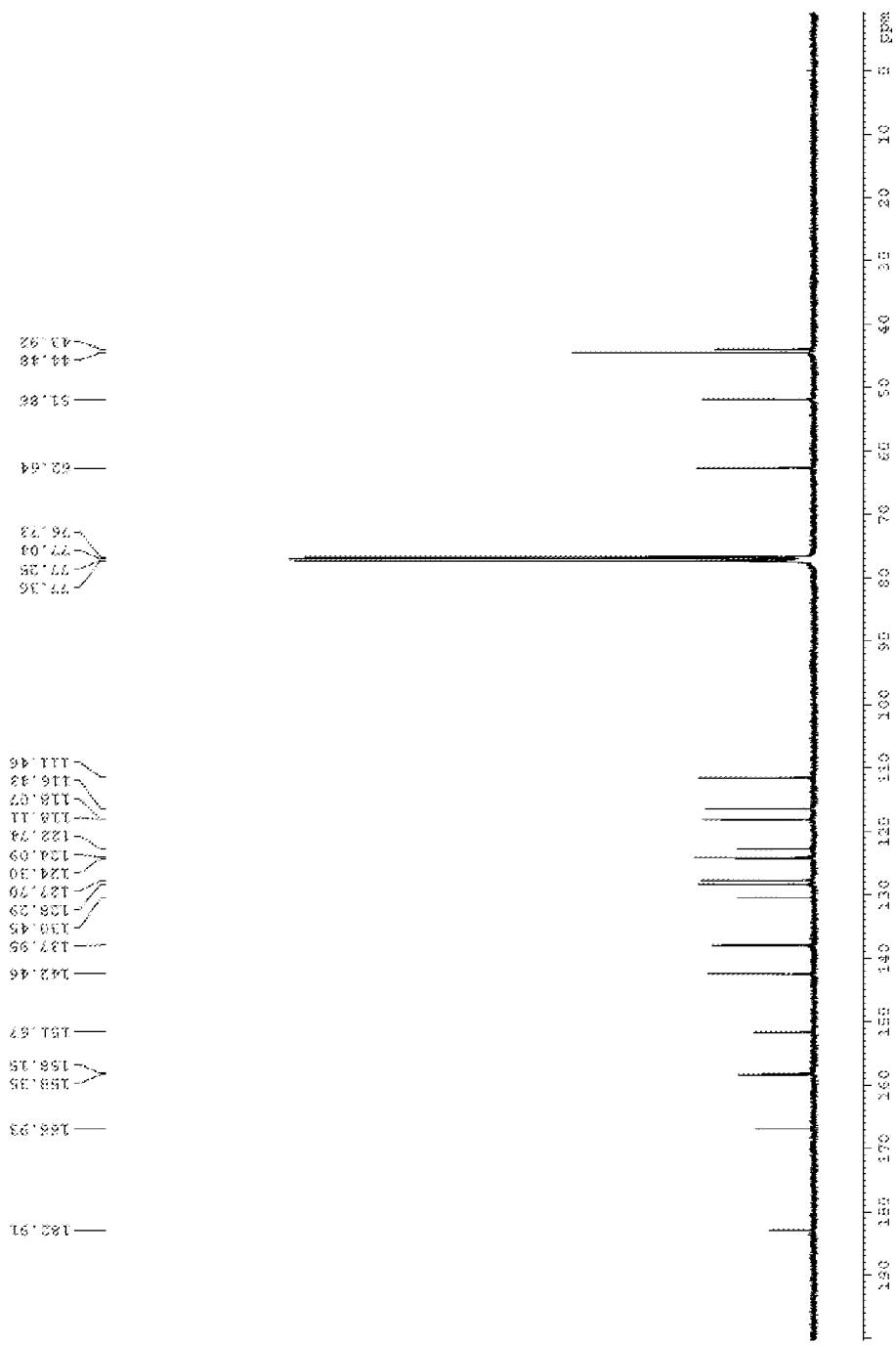
FIG. 4 is $^{13}$C NMR spectra of compound 2 in deuterated chloroform.

In order to understand the present invention, the following examples are further described in conjunction with the present invention: the examples are illustrative, not limitative, and the scope of the invention are not to be limited by the following examples.

Example 1

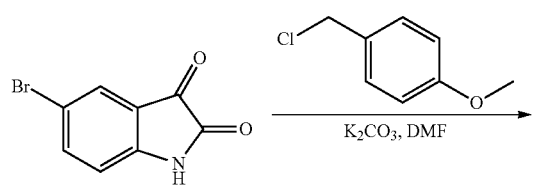

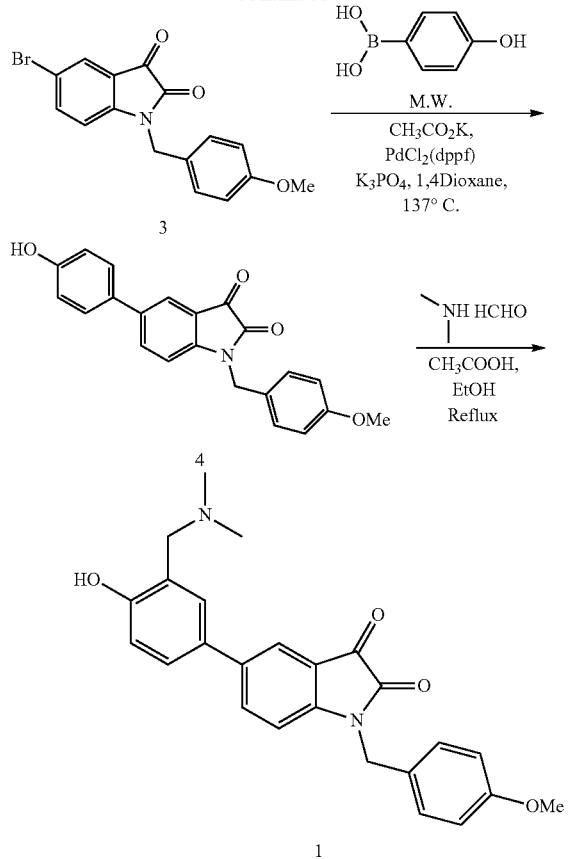

Synthesis of Compound 3

Into a 25 ml round-bottom flask is added 1 g of 5-bromoisatin, 4 ml of DMF, 4.83 g of potassium carbonate and 0.83 g of p-methoxy benzyl chloride in this sequence. The mixture is stirred overnight at room temperature, and the reaction is complete as indicated by TLC. 20 ml of water is added into the reaction mixture, and red solid precipitates after stirring for 10 minutes. After filtering and drying in air to obtain a red solid of 1.38 g, 90% yield. $^1$H NMR (400 MHz, d6-DMSO) δ 7.76 (d, J=8.4 Hz, 1H) 7.73 (s, 1H), 7.36 (d, J=8.4 Hz, 2H), 6.94 (d, J=8.4 Hz, 1H), 6.91 (d, J=8.4 Hz, 2H), 4.84 (s, 2H), 3.73 (s, 3H).

Synthesis of Compound 4

1 g of compound 3 and 0.48 g of p-hydroxyphenylboronic acid are sequentially added into 20 ml microwave tube, 0.43 g of potassium acetate and 0.24 g of [1,1'-bis(diphenylphosphine)ferrocene]dichloropalladium(II) are added into the tube. 1, 4-Dioxane is added to dissolve the mixture. Argon is filled for 5 minutes, and the tube is sealed, the reaction conditions are as follows: the temperature is 137° C., and the time is 1 hour, the pre-stirring is carried out for 30 seconds, the microwave absorption level is normal, and the reaction is complete as indicated by TLC. 50 ml of water is added into the system, stirring for 10 minutes, and the mixture is extracted for three times (50 ml each time). The combined organic phase is washed with brine for three times, dried over anhydrous sodium sulfate, filtered and concentrated under reduced pressure to afford the crude product, which was purified by flash column chromatography using PE:EA=3:1 as eluent to obtain the product. The product is further recrystallized from dichloromethane and hexane to obtain 0.75 g of brown solid, wherein the yield is 74%. $^1$H NMR (400 MHz, d6-DMSO) δ 9.58 (s, 1H), 7.79 (d, J=8.4 Hz, 1H), 7.71 (s, 1H), 7.46 (d, J=8.4 Hz, 2H), 7.38 (d, J=8.8 Hz, 2H), 7.02 (d, J=8.0 Hz, 1H), 6.91 (d, J=6.8 Hz, 2H), 6.81 (d, J=6.8 Hz, 2H), 4.86 (s, 2H), 3.72 (s, 3H).

(3) Synthesis of Compound 1

60 mg of compound 4 was added into a 25 ml round bottom flask, and ethanol was added for dissolving. Then 146 µl of dimethylamine, 66 µl of formaldehyde and 50 µl of glacial acetic acid were sequentially added, and refluxing overnight. 10 ml of water was added into the system, stirring for 10 minutes, and the mixture was extracted for three times (20 ml each time). The combined organic phase was washed with brine for three times, dried over anhydrous sodium sulfate, filtered and concentrated under reduced pressure to afford the crude product, which was purified by flash column chromatography using DCM:MeOH=20:1 as eluent to obtain the product. The product is further recrystallized from dichloromethane and hexane to obtain 43 mg of orange red solid, wherein the yield is 62%. NMR (400 MHz, CDCl$_3$) δ 2.35 (s, 6H), 3.32 (s, 1H), 3.68 (s, 2H), 3.79 (s, 3H), 4.89 (s, 2H), 6.82 (d, 1H, J=8.0 Hz), 6.86-6.89 (m, 3H), 7.09 (s, 1H), 7.28-7.30 (m, 3H), 7.63 (d, 1H, J=8.0 Hz), 7.76 (s, 1H). $^{13}$C NMR (100 MHz, CDCl3) δ 43.6, 44.5, 55.3, 62.9, 111.3, 114.5, 116.7, 118.1, 122.5, 123.2, 126.4, 126.6, 126.8, 129.0, 129.8, 136.0, 137.3, 149.1, 158.3, 158.4, 159.5, 183.7. HRMS (ESI-TOF) m/z calcd. for C$_{25}$H$_{24}$N$_2$O$_4$ [M+H]+: 417.1809, found 417.1816.

Example 2

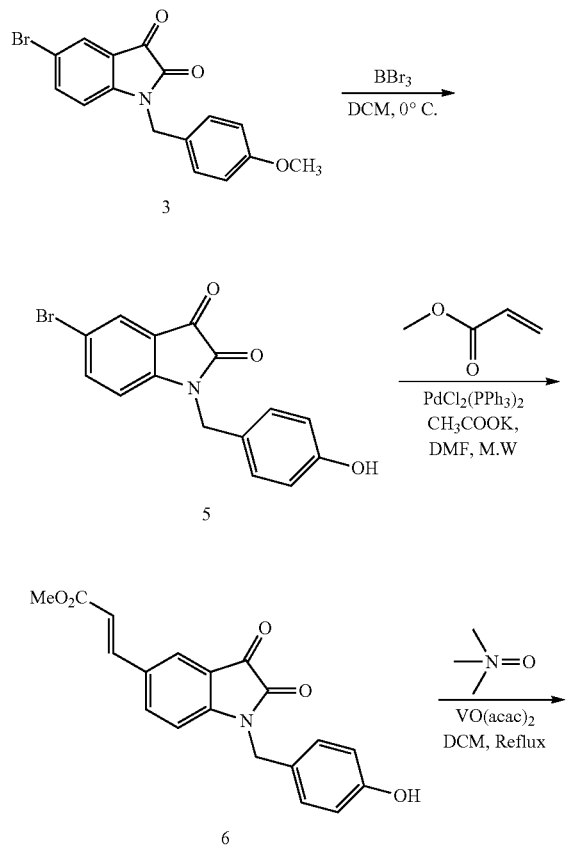

3

5

6

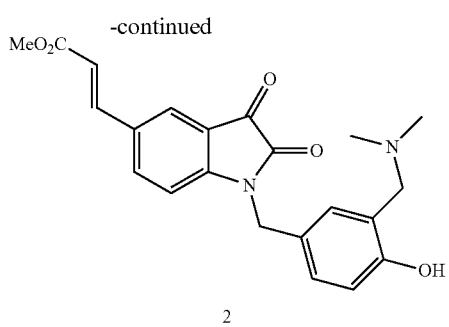

2

Synthesis of Compound 5

200 Mg of compound 3 was added into a dried 50 ml round bottom flask, and 1 ml of DCM was added to dissolve the compound. Then 0.12 ml of a 1 M BBr$_3$ in dichloromethane solution was added under the protection of argon. After stirring for half an hour at 0° C., the reaction was complete as indicated by TLC. 10 ml of saturated aqueous sodium bicarbonate solution was added into the system, and stirring for 10 minutes. Then the mixture was extracted with DCM. The combined organic phase was washed with brine for three times, dried over anhydrous sodium sulfate, filtered and concentrated under reduced pressure to afford the crude product, which was purified by flash column chromatography using PE:EA=3:1 as eluent to obtain the product. The product is further recrystallized from dichloromethane and hexane to obtain 243 mg of brownish red solid, wherein the yield is 84%. $^1$H NMR (400 MHz, d6-DMSO) δ 9.43 (s, 1H), 7.76 (d, J=8.4 Hz, 1H), 7.73 (s, 1H), 7.23 (d, J=8.4 Hz, 2H), 6.94 (d, J=8.4 Hz, 1H), 6.72 (d, J=8.4 Hz, 2H), 4.78 (s, 2H).

Synthesis of Compound 6

300 Mg of compound 5 and 102 µl of methyl acrylate are sequentially added into 5 ml microwave tube, 121 mg of potassium acetate and 32 mg of [1,1'-bis(diphenylphosphine)ferrocene]dichloropalladium(II) were added into the tube. DMF was added to dissolve the mixture. Argon was filled for 5 minutes, and the tube was sealed, the reaction conditions were as follows: the temperature was 137° C., and the time is 1 hour, the pre-stirring was carried out for 30 seconds, the microwave absorption level was normal, and the reaction was complete as indicated by TLC. 20 ml of water was added into the system, stirring for 10 minutes, and the mixture was extracted with DCM. The combined organic phasewas washed with brine for three times, dried over anhydrous sodium sulfate, filtered and concentrated under reduced pressure to afford the crude product, which was purified by flash column chromatography using PE:EA=3:1 as eluent to obtain the product. The product is further recrystallized from dichloromethane and hexane to obtain 281 mg of brownish red solid, wherein the yield is 92%. $^1$H NMR (400 MHz, CDCl$_3$) δ 7.78 (s, 1H), 7.57-7.64 (m, 2H), 7.22 (d, J=8.4 Hz, 2H), 6.85-6.81 (m, 3H), 6.35 (d, J=16.0 Hz, 1H), 4.97 (s, 1H), 4.87 (s, 2H), 3.81 (s, 3H).

Synthesis of Compound 2

To a dried 25 ml round bottom flask was added 50 mg of compound 6, 34 mg of trimethylamine nitrogen oxide and 5 mg of vanadyl acetylacetonate. The mixture was stirred and refluxed overnight under the protection of argon, and the reaction was completely as indicated by TLC. The reaction was cooled down to r.t. 10 ml of water was added into the system, stirring for 10 minutes, and the mixture was extracted with DCM. The combined organic phase was washed with brine for three times, dried over anhydrous sodium sulfate, filtered and concentrated under reduced pressure to afford the crude product, which was purified by flash column chromatography using DCM:MeOH=20:1 as eluent to obtain the product. The product is further recrystallized from dichloromethane and hexane to obtain 38 mg of a red solid, wherein the yield is 65%. $^1$H NMR (400 MHz, CDCl$_3$) δ 2.30 (s, 6H), 3.60 (s, 2H), 3.80 (s, 3H), 4.82 (s, 2H), 6.35 (d, 1H, J=16.0 Hz), 6.78 (d, 1H, J=8.0 Hz), 6.87 (d, 1H, J=8.0 Hz), 6.93 (s, 1H), 7.14 (d, 1H, J=8.4 Hz), 7.57-7.64 (m, 2H), 7.77 (s, 1H). $^{13}$C NMR (100 MHz, CDCl$_3$) δ 43.9, 44.5, 51.9, 62.6, 111.5, 116.4, 118.0, 118.1, 122.7, 124.1, 124.3, 127.7, 128.3, 130.4, 137.9, 142.5, 151.7, 158.2, 158.4, 166.9, 182.9. HRMS (ESI-TOF) m/z calcd. for C$_{22}$H$_{22}$N$_2$O$_5$ [M+Na]+: 417.1421, found 417.1425.

Anti-Tumor Activity Determination Method

1. Solution Preparation Method

Preparation of low glucose DMEM medium: MEM medium (Hyclone) was purchased with low glucose, 500 mL per bottle, 10% fetal bovine serum and 1% streptomycin solution were added in it. That is, 50 mL of fetal bovine serum and 5 mL of streptomycin were added to each flask of the medium. The preparation of the medium was carried out in an ultra-clean workbench and stored in a refrigerator at 4° C.

Preparation of DMEM/F-12 medium: MEM/F-12 medium (Hyclone) was purchased, 500 mL per bottle, 10% fetal bovine serum and 1% streptomycin solution were added in it. That is, 50 mL of fetal bovine serum and 5 mL of streptomycin were added to each flask of the medium. The preparation of the medium was carried out in an ultra-clean workbench and stored in a refrigerator at 4° C.

Preparation of PBS buffer: Sodium chloride 8 g, potassium chloride 0.2 g, disodium hydrogen phosphate dodecahydrate 2.9 g, potassium dihydrogen phosphate 0.2 g and purified water 800 mL were placed into a 1000 mL conical flask, the mixture was stirred and dissolved to a volume of 1000 mL. After autoclaving, PBS buffer was stored in a refrigerator at 4° C.

Preparation of MTT solution: 0.5 g MTT dry powder was dissolved in 100 mL PBS buffer. After sterilizing by filtration through a 0.22 μM filter, it was stored in a refrigerator at −12° C.

2. Specific Steps of Anti-Tumor Activity Determination

Three kinds of tumor cells were used in the antitumor activity assay of the present invention: human liver cancer cells (HepG2), human leukemia cells (K562) and human colon cancer cells (HCT116).

Activity Test Using Human Liver Cancer HepG2 Cells

The human liver cancer cells (HepG2) were grown in DMEM medium supplemented with 10% fetal bovine serum, 1% penicillin/streptomycin and were cultured in an incubator of 5% CO$_2$ at 37° C. The method comprises the following steps:

(1) After counting the cells with a hemocytometer, dilute it to a density of 5×10$^4$ cells/mL with low glucose DMEM medium;

(2) 100 μl cell suspension was added in each well of 96-well plates and incubated at 37° C. for 24 h;

(3) The compound to be tested was diluted to five concentrations: 2 mM, 200 μM, 20 μM, 2 μM, 0.2 μM. Then, 0.5 μL compound of different concentrations was added to the well and incubated at 37° C. for another 48 h;

(4) MTT (5 mg/ml) was added to each well and the plate was further incubated for 4 h at 37° C.;

(5) Dissolving the cells with DMSO, and the OD values were measured at 490 nm and 630 nm by a microplate reader;

(6) Process the data by calculating the IC$_{50}$ value based on the OD values.

Activity test using human leukemia K562 cells

The human leukemia cells (K562) were grown in RPMI1640 medium supplemented with 10% fetal bovine serum, 1% penicillin/streptomycin and were cultured in an incubator of 5% CO$_2$ at 37° C.

The method comprises the following steps:

(1) After counting the cells with a hemocytometer, dilute it to a density of 5×10$^4$ cells/mL with RPMI1640 medium;

(2) 100 μl cell suspension was added in each well of 96-well plates and incubated at 37° C. for 2 h;

(3) The compound to be tested was diluted to five concentrations: 2 mM, 200 μM, 20 μM, 2 μM, 0.2 μM. Then, 0.5 μL compound of different concentrations was added to the well and incubated at 37° C. for another 48 h;

(4) MTT (5 mg/ml) was added to each well and the plate was further incubated for 4 h at 37° C.;

(5) Dissolving the cells with DMSO, and the OD values were measured at 570 nm and 630 nm by a microplate reader;

(6) Process the data by calculating the IC$_{50}$ value based on the OD values.

Activity test using human colon cancer HCT116 cells

The human colon cancer cells (HCT116) were grown in DMEM/F-12 medium supplemented with 10% fetal bovine serum, 1% penicillin/streptomycin and were cultured in an incubator of 5% CO$_2$ at 37° C. The method comprises the following steps:

(1) After counting the cells with a hemocytometer, dilute it to a density of 5×10$^4$ cells/mL with DMEM/F-12 medium;

(2) 100 μl cell suspension was added in each well of 96-well plates and incubated at 37° C. for 24 h;

(3) The compound to be tested was diluted to five concentrations: 2 mM, 200 μM, 20 μM, 2 μM, 0.2 μM. Then, 0.5 μL compound of different concentrations was added to each well and incubated at 37° C. for another 48 h;

(4) MTT (5 mg/ml) was added to the well and the plate was further incubated for 4 h at 37° C.;

(5) Dissolving the cells with DMSO, and the OD values were measured at 490 nm and 630 nm by a microplate reader;

(6) Process the data by calculating the IC$_{50}$ value based on the OD values.

What is claimed is:

1. An isatin derivative having the following general structure I: wherein R$^1$ is alkyl, alkoxy, trifluoromethyl or aryl

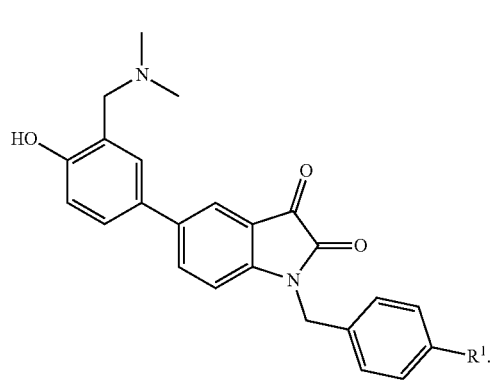

2. An isatin derivative having the following general structure II: wherein, $R^2$ is a hydrogen or an alkyl, and $R^3$ is a group connected to any position of the benzene ring, wherein the group is an α, β-unsaturated ester group, an alkyl group, an alkoxy group, a halogen group, a carboxyl group, a cyano group or an aryl group

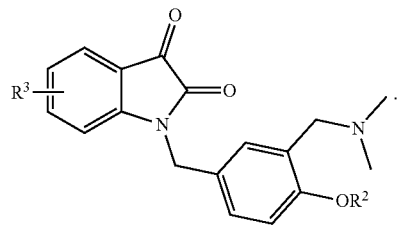

II

3. A method of preparing the isatin derivative of claim 1 comprising: converting compound III into compound IV by Suzuki coupling reaction:

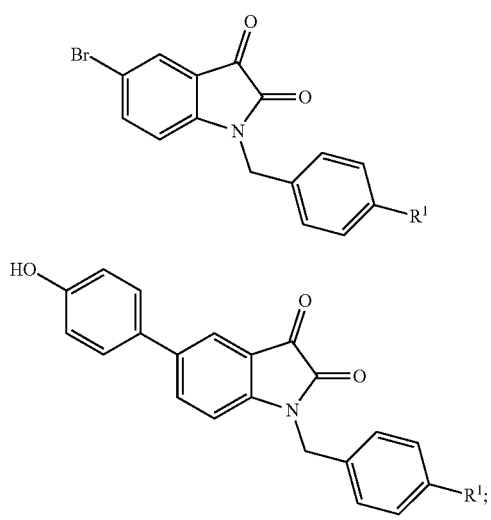

III

IV and
converting compound IV into the final product I through Mannich-like reaction with dimethyl amine, formaldehyde under the catalysis of acetic acid.

4. A method of preparing the isatin derivative of claim 2, comprising
removing methyl group of compound V under the action of boron tribromide to obtain compound VI:

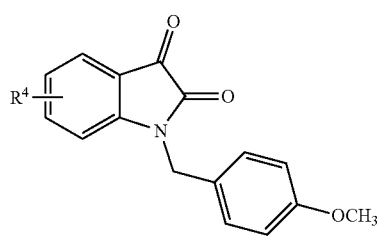

V

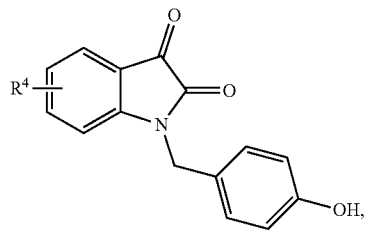

VI and then under the catalysis of a vanadium catalyst, reacting compound VI with trimethylamine nitrogen oxide to obtain VII,

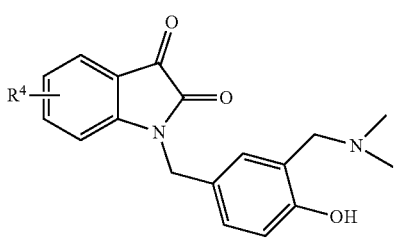

VII and
finally reacting compound VII with an alkyl iodide $R^3I$ to obtain product III.

5. The isatin derivative of claim 1, represented by the following structure:

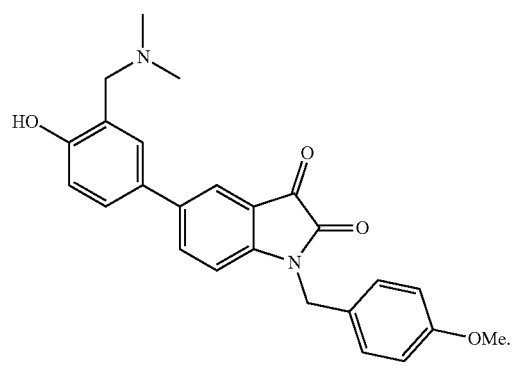

1

6. The isatin derivative of claim 2, represented by the following structure:

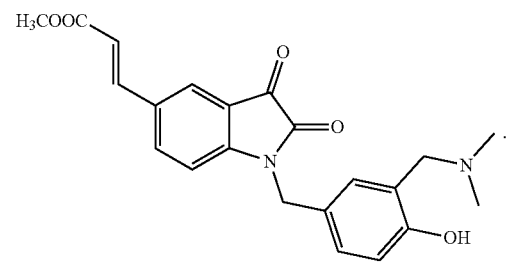

2

7. A method of treating leukemia, colon cancer and liver cancer comprising administering the isatin derivative of claim 1.

8. A method of treating leukemia, colon cancer and liver cancer comprising administering the isatin derivative of claim 2.

9. A method of treating leukemia, colon cancer and liver cancer comprising administering the isatin derivative of claim 5.

10. A method of treating leukemia, colon cancer and liver cancer comprising administering the isatin derivative of claim 6.

11. A pharmaceutical composition comprising the isatin derivative of claim 1.

12. A pharmaceutical composition comprising the isatin derivative of claim 2.

13. A pharmaceutical composition comprising the isatin derivative of claim 5.

14. A pharmaceutical composition comprising the isatin derivative of claim 6.

* * * * *